United States Patent [19]

Demmering et al.

[11] Patent Number: 5,364,986
[45] Date of Patent: Nov. 15, 1994

[54] PROCESS FOR THE PRODUCTION OF FATTY ALCOHOLS

[75] Inventors: Guenther Demmering, Solingen; Stephan Heck, Pulheim; Lothar Friesenhagen, Duesseldorf, all of Germany

[73] Assignee: Henkel Kommanditgesellschaft auf Aktien, Duesseldorf, Germany

[21] Appl. No.: 150,931

[22] Filed: Nov. 10, 1993

[30] Foreign Application Priority Data

Dec. 16, 1992 [DE] Germany ............... 4242466

[51] Int. Cl.⁵ .................. C07C 31/125; C07C 31/20; C07C 29/136
[52] U.S. Cl. ..................................... 568/885; 568/864
[58] Field of Search ................. 568/885, 864

[56] References Cited

U.S. PATENT DOCUMENTS

| | | | |
|---|---|---|---|
| 4,918,248 | 4/1990 | Hattori et al. | 568/885 |
| 4,942,266 | 7/1990 | Fleckenstein et al. | 568/885 |
| 4,982,020 | 1/1991 | Carduck et al. | 568/864 |
| 5,233,100 | 8/1993 | Tabata et al. | 568/885 |

FOREIGN PATENT DOCUMENTS

| | | |
|---|---|---|
| 0230971 | 8/1987 | European Pat. Off. . |
| 0254189 | 1/1988 | European Pat. Off. . |
| 0280982 | 9/1988 | European Pat. Off. . |
| 2250287 | 6/1992 | United Kingdom ............... 568/885 |
| 9204119 | 3/1992 | WIPO . |

*Primary Examiner*—Joseph E. Evans
*Attorney, Agent, or Firm*—Wayne C. Jaeschke; John E. Drach; Henry E. Millson, Jr.

[57] ABSTRACT

$C_{8-22}$ fatty alcohols are produced by a process which comprises contacting a triglyceride with hydrogen in the presence of a copper-zinc catalyst and in a reaction zone. The hydrogen pressure in the reaction zone is from about 200 to about 280 bar, the temperature of the entrance of the reaction zone is from about 200° C. to about 230° C., and the temperature of the exit of the reaction zone is from about 190° C. to about 220° C. The amount of 1,2-propanediol formed is optimized by the lower temperature of the exit portion of the reaction zone.

15 Claims, No Drawings

PROCESS FOR THE PRODUCTION OF FATTY ALCOHOLS

BACKGROUND OF THE INVENTION

1. Field of the Invention

This invention relates to a process for the production of fatty alcohols, in which natural fats and oils are subjected to catalytic high-pressure hydrogenation in a tube bundle reactor.

2. Description of the Related Art

Fatty alcohols are normally produced from fatty acid methyl esters which are subjected to high-pressure hydrogenation in the presence of heterogeneous copper-chromium spinels, so-called Adkins catalysts. Although fatty acids may be used instead of the esters, this does mean that the stability of the catalysts has to meet particular requirements.

A particularly elegant method for the production of fatty alcohols is the direct hydrogenation of the natural fats and oils on which they are based. A process such as this also affords advantages by reducing the outlay on equipment and improving profitability because the starting materials used do not have to be so highly refined and, instead of the glycerol formed in the transesterification of fatty acid methyl esters, 1,2-propanediol is formed as a valuable secondary product.

The processes of the prior art have the disadvantage that the valuable 1,2-propanediol is not the only secondary product of the hydrogenation reaction. Instead, a complex mixture is obtained which, besides propane, propene, propanols and other substances, contains propanediols as one of many components so that isolation is out of the question on economic grounds. Accordingly, the profitability of processes for the direct hydrogenation of natural fats and oils is critically linked with the question of how selectively 1,2-propanediol is formed as a secondary product.

Accordingly, the problem addressed by the present invention was to develop a process for the direct hydrogenation of triglycerides which would be distinguished by particularly high selectivity for the formation of 1,2-propanediol as a secondary product.

SUMMARY OF THE INVENTION

The present invention relates to a process for the production of $C_{8-22}$ fatty alcohols, in which triglycerides, such as natural fats and oils, are hydrogenated in a reaction zone, such as in a tube bundle reactor, in the presence of a copper-zinc catalyst. The hydrogen pressure in the reaction zone is from about 200 to about 280 bar, the temperature of the entrance of the reaction zone is from about 200° C. to about 230° C., and the temperature of the exit of the reaction zone is from about 190° C. to about 220° C. The amount of 1,2-propanediol formed is optimized by reducing the temperature of the exit of the reaction zone to a range of from about 190° C. to about 220° C.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

It has surprisingly been found that the selectivity for 1,2-propanediol in the direct hydrogenation of triglycerides can be distinctly improved if copper-zinc catalysts are used and if the heat of reaction is dissipated as quickly as possible during the reaction. It has proved to be particularly advantageous in this regard to establish a reaction zone entry temperature of 210° to 230° C. and a reactor exit temperature of 205° to 215° C. The hydrogen pressure can be from 200 to about 280 bar.

Natural fats and oils are suitable starting materials for the process according to the invention. Natural fats and oils are understood to be triglycerides which may contain small quantities of partial glycerides and optionally free fatty acids. Typical examples are palm oil, palm kernel oil, coconut oil, olive oil, sunflower oil, rapeseed oil, cottonseed oil, peanut oil, linseed oil, coriander oil, soybean oil, lard and beef tallow which exclusively or predominantly contain $C_{8-22}$ fatty acids. Other suitable starting materials are of course correspondingly synthesized triglycerides. The iodine value of the starting materials used is largely uncritical because the catalyst used provides for the saturation of double bonds present in the fatty chain.

Copper-zinc catalysts for the production of $C_{8-22}$ fatty alcohols by hydrogenation of natural fats and oils are known. They are produced by:

a) adding alkali metal carbonate compounds to aqueous solutions containing water-soluble copper(II) and zinc(II) salts to a pH value of 6 to 10, b) separating and drying the resulting precipitate of basic copper(II) and zinc(II) carbonate, c) calcining the dried catalyst for 1 to 60 minutes at temperatures of 400° to 600° C. and d) subsequently reducing the calcined catalyst to particulate form.

In the context of the invention, water-soluble copper(II) and zinc(II) salts are understood to be the sulfates, nitrates and halides free from or containing water of crystallization. It is preferred to use copper(II) nitrate and zinc(II) nitrate because the anion can be washed out particularly easily after precipitation of the hydroxides. The aqueous solutions may contain the water-soluble copper(II) and zinc(II) salts in molar ratios or 1:10 to 10:1. Particularly active catalysts are obtained with molar ratios of 1:2 to 2:1 and, more particularly 1:1.

In the context of the invention, alkali metal carbonate compounds are understood to be aqueous 0.05 to 50% by weight and preferably 25 to 50% by weight solutions of lithium, potassium or, in particular, sodium carbonate or sodium hydrogen carbonate.

For the further stages of the production process, the alkali metal compound is added in portions to the aqueous solution containing the copper(II) and zinc(II) salts at 50 to 90° C. until a pH value of at least 6 is reached. A pH value in the range from 8 to 9 has proved to be optimal for precipitation. The mixture of basic copper(II) and zinc(II) carbonate formed is separated from the aqueous solution, for example by filtration or centrifugation, washed and dried.

After the precipitation step, the dried catalyst may be calcined for 1 to 60 minutes and preferably for 5 to 15 minutes at temperatures in the range from 400° to 600° C. and preferably at temperatures in the range from 450° to 550° C. The basic copper/zinc carbonates are converted into irregular crystallite fragments which may then readily be compacted. Alternatively, the catalyst may be activated in known manner by treatment with hydrogen under reducing conditions.

For use in the tube bundle reactor, the catalyst has to be reduced to a particulate form. To this end, the catalyst may be converted into cylindrical pellets, for example in a rotary pelleting machine, or into cylindrical extrudates in a screw extruder preceded by a perforated disk.

Another important criterion for the practical application of the process according to the invention lies in the use of tube bundle reactors which have the advantage over tube reactors of a larger surface and hence easier heat exchange. Thermal oil is preferably used as the cooling medium which is circulated on the countercurrent principle. The surface on which heat exchange can take place does of course increase with the number of tubes present in the bundle. A number of 15 to 70 and preferably 25 to 60 tubes with an optimal length of 5 to 12 m and preferably 6 to 9 m for a preferred internal diameter of 3 to 9 cm and, more particularly, 5 to 7 cm may be regarded as appropriate.

In order to increase the selectivity for 1,2-propanediol, the lower part of the tube bundle reactor has to be cooled during the hydrogenation of the fats and oils to such an extent that the product leaving the reactor has a temperature of 190° to 220° C. To this end, it is advisable to introduce the cooling medium at the reactor exit with a temperature of 180° to 200° C. The low entry temperature of the cooling medium reciprocally provides for a relatively high entry temperature of 200° to 230° C. of the triglyceride to be hydrogenation which is also of advantage in regard to higher selectivity for 1,2-propanediol.

The 1,2-propanediol may be separated from the fatty alcohols by methods known per se, for example by distillation.

The conversion achieved in the process according to the invention is between 90 and 95% of the theoretical, based on fatty alcohol, while the selectivity for 1,2-propanediol of approximately 90% of the theoretical are obtained. The fatty alcohols may be used, for example, for further derivatization for the synthesis of anionic or nonionic surfactants while the 1,2-propanediol may be used as a component for the production of polyesters.

The following Examples are intended to illustrate the invention without limiting it in any way.

EXAMPLE 1

A) Production of the catalyst:

In a heatable 450 liter stirred vessel, 24.6 kg (102 mol) copper(II) nitrate trihydrate and 30.3 kg (102 mol) zinc-(II) nitrate hexahydrate were dissolved in 204 l fully deionized water. 43.1 kg (407 mol) 50% by weight sodium carbonate solution were introduced into a second, 140 liter vessel. Both solutions were first heated to 70° C. and the sodium carbonate solution was subsequently pumped over a period of 30 minutes (throughput rate 110 l/h) into the solution of the two nitrates, resulting in the formation of a precipitate consisting of the dibasic carbonates of copper and zinc. On completion of the precipitation step, the precipitate was stirred in its mother liquor for 30 minutes at 90° C. to achieve a uniform particle size distribution with a sharp maximum. The solid was then filtered off and washed with fully deionized water to a residual nitrate content of less than 50 ppm in the effluent. The filter cake was placed on shelves and dried in a drying cabinet for 12 h at 120° C. to a residual moisture content below 1% by weight. The basic copper/zinc carbonate was obtained in the form of dry brown-black powder. The powder was ground and subsequently calcined in air in a rotary kiln over a period of 8 minutes at a temperature $T_c$ of 550° C. The calcined powder was then transferred to a rotary pelleting machine in which it was converted into cylinders measuring 4×4 mm which had an average fracture hardness of 4 to 6 kp. The precipitate above, consisting of the dibasic carbonates of copper and zinc, obviously provide a catalyst wherein the metals present consist of copper and zinc.

EXAMPLE 2

The tests were carried out in a V4A steel tube bundle reactor comprising 31 tubes (length 6 m, internal diameter 6.5 cm). The starting material used was refined palm kernel oil (saponification value 244) having the following fatty acid composition:

| | |
|---|---|
| Caproic acid | 1% by weight |
| Capric acid | 4% by weight |
| Caprylic acid | 5% by weight |
| Lauric acid | 50% by weight |
| Myristic acid | 15% by weight |
| Palmitic acid | 7% by weight |
| Stearic acid | 2% by weight |
| Oleic acid | 15% by weight |
| Linoleic acid | 1% by weight |

The throughput amounted to 800 l/h and the volume of hydrogen circulated to 20–30 $Dm^3/h$. Pellets produced as described in Example A) were used for the catalyst bed. Thermal oil was used as the medium for the cooling circuit. The hydrogen pressure was 270 bar. Before the beginning of tests, the catalyst bed was activated in a stream of hydrogen at 215° C.

Particulars of the test procedure and the characteristic data of the products are set out in Table 1.

TABLE 1

Direct Hydrogenation of Refined Palm Kernel Oil

| Ex. | T(Reactor) E °C. | T(Reactor) Et. °C. | T(Cooling med.) E °C. | T(Cooling med.) Et. °C. | S.V. | PD % | S % |
|---|---|---|---|---|---|---|---|
| 1 | 212 | 205 | 190 | 206 | 21.6 | 9.0 | 88.2 |
| C1 | 215 | 223 | 215 | 230 | 0.6 | 1.7 | 16.7 |
| C2 | 215 | 216 | 205 | 216 | 1.9 | 4.2 | 41.2 |

Legend:
T(Reactor) = Reactor temperature
T(Cooling med.) = Temperature of cooling medium
E = Entry
Et. = Exit
S.V. = Saponification value of the hydrogenation product
PD = Yield of 1,2-propanediol (% by weight)
S = Selectivity, based on propane-1,2-diol (% of the theoretical)

We claim:

1. A process for the production of $C_{8-22}$ fatty alcohol comprising contacting a triglyceride with hydrogen in the presence of a copper-zinc catalyst, wherein copper and zinc are the only metallic components thereof, and in a reaction zone having an entrance and exit wherein the hydrogen pressure in said reaction zone is from about 200 to about 280 bar, the temperature of the entrance of said reaction zone is from about 200° C. to about 230° C., and the temperature of the exit of said zone is from about 190° C. to about 220° C.

2. The process of claim 1 wherein said copper-zinc catalyst is a calcined catalyst.

3. The process of claim 1 wherein said triglyceride is a natural fat or oil.

4. The process of claim 1 wherein said triglyceride is selected from the group consisting of palm oil, palm kernel oil, coconut oil, olive oil, sunflower oil, rapeseed oil, cottonseed oil, peanut oil, linseed oil, coriander oil, soybean oil, and lard and beef tallow.

5. The process of claim 4 wherein said triglyceride is palm kernel oil.

6. The process of claim 1 wherein said temperature of the entrance of said reaction zone is from about 210° C. to about 230° C.

7. The process of claim 1 wherein said temperature of the exit of said reaction zone is from about 205° C. to about 215° C.

8. The process of claim 1 wherein the temperature of the entrance of said reaction zone is from about 210° C. to about 230° C., and the temperature of the exit of said reaction zone is from about 205° C. to about 215° C.

9. The process of claim 1 wherein said reaction zone is a tube bundle reactor, and the catalyst is in particulate form.

10. The process of claim 2 wherein the molar ratio of copper to zinc in the catalyst is from about 1:10 to about 10:1.

11. The process of claim 10 wherein said ratio is from about 1:2 to about 2:1.

12. The process of claim 11 wherein said ratio is about 1:1.

13. The process of claim 1 wherein the copper-zinc catalyst is a calcined catalyst having a molar ratio of copper to zinc of from about 1:10 to about 10:1; the temperature of the entrance of said reaction zone is from about 210° C. to about 230° C.; and the temperature of the exit of said reaction zone is from about 205° C. to about 215° C.

14. The process of claim 13 wherein said molar ratio of copper to zinc is from about 1:2 to about 2:1.

15. The process of claim 13 wherein said reaction zone is a tube bundle reactor, and the catalyst is in particulate form.

* * * * *